United States Patent [19]

Heise et al.

[11] 4,153,798

[45] May 8, 1979

[54] PROCESS FOR THE MANUFACTURE OF 5-ACETOACETYLAMINO-BENZIMIDAZO-LONE

[75] Inventors: Hartmut Heise, Bad Soden am Taunus; Bernd Leibmann, Darmstadt; Dieter Mörler, Liederbach; Eberhard Ritter, Walldorf; Wilfried Sahm, Kelkheim, all of Fed. Rep. of Germany

[73] Assignee: Hoechst Aktiengesellschaft, Frankfurt, Fed. Rep. of Germany

[21] Appl. No.: 780,221

[22] Filed: Mar. 22, 1977

[30] Foreign Application Priority Data

Mar. 24, 1976 [DE] Fed. Rep. of Germany ....... 2612391

[51] Int. Cl.$^2$ ............................................ C07D 235/26
[52] U.S. Cl. ................................................... 548/305
[58] Field of Search ................................... 548/305

[56] References Cited

U.S. PATENT DOCUMENTS

| 1,982,675 | 12/1934 | Law ................................. 260/562 K |
| 2,152,132 | 3/1939 | Boese ........................... 260/562 K X |
| 3,555,003 | 1/1971 | Ribka .................................... 260/157 |
| 3,963,694 | 6/1976 | Mory et al. ........................... 260/154 |
| 4,087,610 | 5/1978 | Sahm et al. ........................... 548/305 |

FOREIGN PATENT DOCUMENTS

| 723057 | 2/1955 | United Kingdom ................ 260/562 K |
| 770263 | 3/1957 | United Kingdom ................ 260/562 K |
| 962227 | 7/1964 | United Kingdom ................ 260/562 K |

*Primary Examiner*—Richard Raymond
*Attorney, Agent, or Firm*—Curtis, Morris & Safford

[57] ABSTRACT

When continuously reacting an aqueous solution of 5-aminobenzimidazolone-(2) or a salt thereof with diketene then 5-acetoacetylamino-benzimidazolone is obtained in a smooth and safe reaction without foaming. The product results in high space-time yield and excellent quality.

8 Claims, No Drawings

PROCESS FOR THE MANUFACTURE OF 5-ACETOACETYLAMINO-BENZIMIDAZOLONE

CROSS-REFERENCE TO RELATED APPLICATION

A process for the manufacture of 5-acetoacetylamino-benzimidazolone-(2) by reaction of 5-aminobenzimidazolone-(2) with diketene has already been proposed, which comprises using the 5-aminobenzimidazolone-(2) in the form of a salt of an acid having a pKa value of from 1 to 7 in an aqueous solution (U.S. Pat. Application Ser. No. 680,719 filed Apr. 27, 1976, now U.S. Pat. 4,087,610). Although this operation mode yields a high-quality reaction product, its performance in industrial practice still creates problems. Since in a side reaction of diketene and hot water carbon dioxide is formed, the rapid diketene feed causes a temporary vigorous carbon dioxide formation with heavy foaming of the reaction mixture and creaming of the reaction product. Therefore, (1) for safety reasons, only relatively small batches can be processed,
(2) excessively large reaction vessels are required in order to take up the foam volume, and
(3) the purification of the exhaust gas requires great apparatus expenditure.

It has now been found that 5-acetoacetylamino-benzimidazolone-(2) is obtained in excellent quality and without encounteringthe above disadvantages, when the reaction of the hot aqueous solution of 5-amino-benzimidazolone-(2) or of one of its salts with diketene is carried out continuously.

Advantageous embodiments of the present invention are the following:

The reaction components diketene and aqueous 5-aminobenzimidazolone solution or 5-aminobenzimidazolone salt solution are introduced simultaneously and continuously into a reactor, and thoroughly mixed. In the same proportion as that of reactant feed, an amount of reaction mixture wherein the reaction product is present in the form of a crystallized suspension is removed. The crystallized final product may be isolated subsequently in batchwise or, advantageously, continuous manner.

Suitable reactors are preferably agitation vessels made from inert materials such as glass, enamel or stainless steel and provided with efficient agitators. The reactants may be fed in according to different methods; preferably, the solution of the amine or salt is fed in via a bottom inlet tube, and the diketene via a cover inlet tube. The reaction product is removed very simply by overflow of the reaction suspension via a lateral tube.

Alternatively, both the reactants, either separately or in blended state already, may be fed in from the bottom or the cover of the vessel, below or onto the surface of the liquid. The product may alternatively be removed either via the bottom outlet by means of a siphon, or through the cover by means of an immersion pump.

Good results are obtained also with the use of a flow tube, preferably provided with stationary mixing devices mounted in its interior. In this case, both the liquid currents are fed in via concentrically arranged tubes provided with outlet nozzles; the diketene preferably flowing in via the inner tube, the solution of the amine or salt maintained at reaction temperature being fed in via the ring slot. Advantageously, the flow tube contains such a number of mixing elements which ensures a thorough homogenization of the reactants. It can be designed as a double-jacket tube which may be heated or cooled according to the requirements.

Alternatively, a circulation reactor, that is, a flow tube without inserted devices but with forced circulation, is suitable as well. In the most simple case, a vertical rectangle formed by tubes may be adequate; the two vertical tubes being designed as heat exchanger, so that heating or cooling is possible. The lower horizontal connection tube contains the inlet for the feed of the amine or salt and a centrifugal pump which supplies the diketene. The upper horizontal tube is provided with an exhaust gas duct and the outlet. The hot solution of amine or salt, as seen in the direction of flow, is fed in before the pump, wherein it is blended with the diketene.

The reaction with diketene may be carried out alternatively in a centrifugal pump used as a mixing device and a reaction tube provided with a pressure control valve connected thereto. In this embodiment, the reactant currents are fed axially to the centrifugal pump running at high speed. The tube flanged to the pump outlet is provided with a pressure control valve at its free end, so that the escaping of gas from the suspension is prevented by an overpressure of 5 to 6 bars. After the valve, the reaction mixture is discharged with pressure release into another vessel where it is continued to be agitated.

The feed of the reactants is dosed by suitable flow meters such as rotameters, or by proportioning pumps, in order to ensure a precise and constant mixing ratio.

The continuous reaction with diketene is carried out with the use of equivalent amounts of the reactants or, preferably, a small excess of diketene (about 5 to 10 mol %). Control of deficiency or excess of amine or salt may be ensured continuously by potentiometric methods.

The throughput rate may vary depending on the requirements and the size of apparatus. An average throughput of from 0.25 to 1 kmol/h is easily obtainable which, in view of the solubility conditions of the starting amine or its salts, represents a flow rate of from about 1000 to 4000 l/h.

The reaction may be carried out at a temperature of from about 30° to 100° C., preferably from about 60° to 95° C.

The temperature of the 5-aminobenzimidazolone solution fed in is advantageously from about 80° to about 100° C. in order to attain a concentration of base as high as possible. Temperature control is ensured either by surface cooling or heating (for example jacket or coil cooling) or, preferably, by feeding in water of corresponding temperature. Since the solution of the amine or salt is advantageously fed in in hot state and the reaction heat has to be dissipated in addition, temperature control is generally ensured by a corresponding amount of cold water.

In order to obtain a good quality of the reaction product, it has proved to be advantageous that the reaction suspension is not immediately chilled but that an elevated temperature, preferably of from 60° to 80° C., is maintained for a certain time. Thus, the 5-acetoacetylamino-benzimidazolone can be isolated in the form of crystals, that is, in a higher concentration than obtainable in the batchwise processes.

Even with the above operation mode, there is formation of carbon dioxide. However, its amount is considerably reduced as compared to the batchwise reaction process. Moreover, the development of gas is slowed down and takes a much longer period of time. In the continuous process, there is neither foam formation nor creaming of the product. The exhaust gas may be purified without special expenditure by washing with a base, e.g. sodium hydroxide solution, in a washing device of small dimensions.

Because of the reduced tendency to side reactions with water, the amount of diketene may be decreased as compared to the batchwise process.

Another important economic advantage resides in the fact that a high product throughput can be obtained with small reaction volumes, and the latter ensure a high degree of operational safety in addition.

As far as salts of 5-aminobenzimidazolone-(2) are used, acids having a pKa value of 1 to 7, preferably 3 to 7, especially 4 to 7 are preferably used. Such acids are, e.g., alkanoic acids of 1 to 4 carbon atoms, oxalic acid or phosphoric acid. The pKa ranges given indicate the dissociation stage of the polybasic acid which is appropriate: for phosphoric acid it is the first, preferably the second stage.

The following examples, in which industrial-grade (about 96%) diketene was used, illustrate the invention.

EXAMPLES

Via the bottom inlet tube of a glass vessel having a capacity of 80 liters, a clarified solution of 150 kg of 5-aminobenzimidazolone in 4200 l of water, which solution has a temperature of 90° C., is fed in at a rate of 2100 l/h with agitation. Simultaneously, via a cover inlet tube, diketene is added at a rate of 50 l/h. Immediately, a colorless precipitate of 5-acetoacetyl-aminobenzimidazolone forms. The suspension thus obtained flows via a lateral tube which limits the reaction volume to 40 l into a 8 $m^3$ agitation vessel of stainless steel containing already 1000 l of water having a temperature of 80° C. The reaction temperature in the glass vessel is maintained at 80°–85° C. by spraying water having a temperature of 5° C. onto the surface of the suspension by means of a spray ring (amount of water about 500–600 l/h). After the reaction is complete, the reaction mixture is cooled to 40° C., and the 5-acetoacetylaminobenzimidazolone is isolated by means of a suitable filter. 550 kg of a reaction product of about 40% strength are thus obtained which may be directly used for pigment synthesis without a further purification step.

After purification in the following washing column, no foreign components can be detected any more in the exhaust gas:
base vessel: 1 $m^3$, washing tower; height 2.50 m, internal width 150 mm; packing: Raschig rings; washing liquid: about 20% aqueous sodium hydroxide solution; circulation rate: 5 $m^3$/h.

Similarly good results are obtained when the reaction conditions listed in the following Table are chosen, or when the reaction is carried out in a flow tube with inserted stationary mixing devices, a circulation reactor with forced pump circulation, or a centrifugal pump with reaction tube containing a pressure valve connected thereto, instead of an agitation vessel.

Table

| No. | Starting product | Concentration of starting product (kg/4200 l) | Rate of feed (l/h) | Diketene feed (l/h) | Reaction temperature (° C.) | (kg) | Yield Control % | % of the Yield |
|---|---|---|---|---|---|---|---|---|
| b) | 5-amino-benzimidazolone | 150 | 4000 | 100 | 80–85 | 610 | 34 | 89 |
| c) | " | 150 | 1000 | 25 | 82 | 430 | 49 | 90 |
| d) | " | 150 | 2000 | 50 | 60 | 580 | 35 | 87 |
| e) | " | 150 | 2000 | 50 | 94 | 520 | 40 | 89 |
| f) | di-(5-aminobenzimidazolone)-sodium phosphate | 225* | 2000 | 75 | 80–85 | 710 | 43 | 87 |
| g) | 5-amino-benzimidazolone acetate | 225* | 2000 | 75 | 80–85 | 700 | 44 | 88 |
| h) | " | 300* | 2000 | 100 | 80–85 | 950 | 44 | 90 |
| i) | " | 300* | 1000 | 50 | 83 | 930 | 46 | 92 |
| j) | " | 225* | 2000 | 75 | 60 | 860 | 36 | 88 |

*calculated on 5-aminobenzimidazolone

We claim:

1. In a process for the production of 5-acetoacetylaminobenzimidazolone-(2) by reacting 5-amino-benzimidazolone-(2) with an excess of diketene in water the improvement comprising reacting continuously an aqueous solution consisting essentially of of 5-aminobenzimidazolone-(2) or of a salt thereof with the diketene at a temperature of 30° to 100° C.

2. A process as claimed in claim 1, wherein the temperature is 60° to 95° C.

3. A process as claimed in claim 1, wherein an excess of 5 to 10 mol % of diketene are added.

4. A process as claimed in claim 1, wherein both reaction components are fed into the vessel continuously.

5. A process as claimed in claim 1, wherein the 5-amino-benzimidazolone-(2) or its salt is fed in as a solution in water having 80° to 100° C.

6. A process as claimed in claim 5, wherein the reaction temperature is controlled by spraying in cold eater.

7. A process as claimed in claim 1, wherein the product suspension is allowed to dwell at a temperature of 60° to 80° C.

8. A process as claimed in claim 1, wherein the product is isolated continuously.

* * * * *